United States Patent [19]

Green

[11] 4,416,685
[45] Nov. 22, 1983

[54] TRIFLUOROETHYL-P-CHLOROPHENYL-CARBAMATE HERBICIDE ANTIDOTE

[75] Inventor: Laddie L. Green, San Jose, Calif.

[73] Assignee: Stauffer Chemical Company, Westport, Conn.

[21] Appl. No.: 335,789

[22] Filed: Dec. 30, 1981

[51] Int. Cl.³ .............................................. A01N 25/32
[52] U.S. Cl. .......................................... 71/95; 71/111
[58] Field of Search ...................................... 71/95, 111

[56] References Cited

U.S. PATENT DOCUMENTS 4,021,224  5/1977  Pallos et al. ............................ 71/88
4,110,105  8/1978  Teach ..................................... 71/95

OTHER PUBLICATIONS

Devlin et al., Weed Research, vol. 19, (1979), pp. 59–61.
Shapiro, Chem. Abst., vol. 55, 13358g.

*Primary Examiner*—Catherine L. Mills
*Attorney, Agent, or Firm*—Leona L. Lauder; Beth Kovitz

[57] ABSTRACT

An herbicide antidote composition comprising:

(a) an herbicidally effective amount of a pyrrolidone compound of the formula

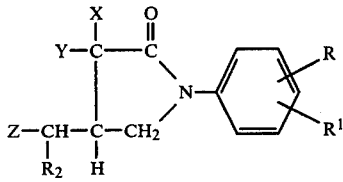

in which
X is hydrogen, chlorine or methyl;
Y is hydrogen, chlorine, or bromine;
Z is chlorine or bromine;
R is hydrogen, alkyl, acetyl, chlorine, bromine, fluorine, iodine, trifluoromethyl, nitro, cyano, alkoxy, alkylthio, alkylsulfinyl, alkylsulfonyl, trifluoromethylthio, trifluoromethylsulfinyl, trifluoromethylsulfonyl, pentafluoropropionamide, or 3-methylureido;
$R_1$ is hydrogen, alkyl, chlorine, or trifluoromethyl; and,
$R_2$ is alkyl or hydrogen; and,
(b) a non-phytotoxic antidotally effective amount of a compound of the formula

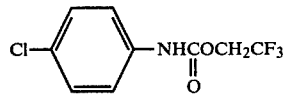

4 Claims, No Drawings

TRIFLUOROETHYL-P-CHLOROPHENYLCARBAMATE HERBICIDE ANTIDOTE

FIELD OF THE INVENTION

This invention relates to herbicide antidotes, and, more particularly, to 2,2-trifluoroethyl p-chlorophenylcarbamate, which is useful as an herbicide antidote.

BACKGROUND OF THE INVENTION

An herbicide is a compound which adversely controls or modifies plant growth, e.g., killing, retarding, defoliating, desiccating, regulating, stunting, tillering, stimulating, and dwarfing. The term "plant" refers to all physical parts of a plant, including seeds, seedlings, saplings, roots, tubers, stems, stalks, foliage, and fruits. "Plant growth" includes all phases of development from seed germination to natural or induced cessation of life.

Herbicides are generally used to control or eradicate weed pests. They have gained a high degree of commercial success because it has been shown that such control can increase crop yield and reduce harvesting costs.

The most popular methods of herbicide application include: pre-plant incorporation into the soil; in-furrow application to seeds and surrounding soil; pre-emergence surface treatment of seeded soil; and post-emergence treatment of the plant and soil.

A manufacturer of an herbicide generally recommends a range of application rates and concentrations calculated to maximize weed control. The range of rates varies from approximately 0.01 to 50 pounds per acre (0.0112 to 56 kilograms per hectare (k/ha)), and is usually in the range of from 0.1 to 25 pounds per acre (0.112 to 28 k/ha). The term "herbicidally effective amount" describes the amount of an herbicide compound which controls or modifies plant growth. The actual amount used depends upon several considerations, including particular weed susceptibility and overall cost limitations.

The most important factor influencing the usefulness of a given herbicide is its selectively towards crops. In some cases, a beneficial crop is susceptible to the effects of the herbicide. In addition, certain herbicidal compounds are phytotoxic to some weed species but not to others. To be effective, an herbicide must cause minimal damage (preferably no damage) to the beneficial crop while maximizing damage to weed species which plague that crop.

To preserve the beneficial aspects of herbicide use and to minimize crop damage, many herbicide antidotes have been prepared. These antidotes reduce or eliminate damage to the crop without substantially impairing the damaging effect of the herbicide on weed species; See, for example, U.S. Pat. Nos. 4,021,224 and 4,021,229 and Belgian Pat. No. 846,894.

The precise mechanism by which an antidote reduces herbicidal crop injury has not been established. An antidote compound may be a remedy, interferent, protectant, or antagonist. As used herein, "antidote" describes a compound which has the effect of establishing herbicide selectivity, i.e., continued herbicidal phytotoxicity to weed species and reduced or non-phytotoxicity to cultivated crop species. The term "antidotally effective amount" describes the amount of an antidote compound which counteracts a phytotoxic response of a beneficial crop to an herbicide.

DESCRIPTION OF THE INVENTION

It has now been discovered that 2,2,2-trifluoroethyl p-chlorophenyl carbamate is an effective antidote for the protection of corn crops from pyrrolidone herbicide injury. This compound has the following formula:

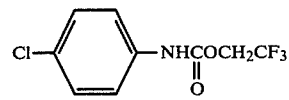

This invention embodies a two-part herbicidal system comprised of:

(a) an herbicidally effective amount of a pyrrolidone compound of the formula

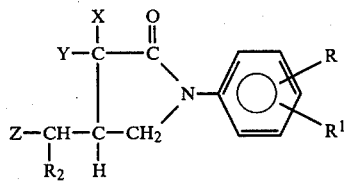

in which
X is hydrogen, chlorine or methyl;
Y is hydrogen, chlorine, or bromine;
Z is chlorine or bromine;
R is hydrogen, alkyl, acetyl, chlorine, bromine, fluorine, iodine, trifluoromethyl, nitro, cyano, alkoxy, alkylthio, alkylsulfinyl, alkylsulfonyl, trifluoromethylthio, trifluoromethylsulfinyl, trifluoromethylsulfonyl, pentafluoropropionamido, or 3-methylureido;
$R_1$ is hydrogen, alkyl, chlorine, or trifluoromethyl; and,
$R_2$ is alkyl or hydrogen; and, (b) a non-phytotoxic antidotally effective amount of a compound of the formula

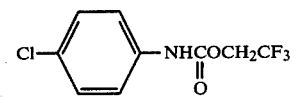

In a preferred embodiment, X is hydrogen, Y is chlorine, Z is chlorine, R is m-trifluoromethyl, $R_1$ is hydrogen and $R_2$ is hydrogen.

This invention also includes the method of establishing herbicidal selectivity which comprises applying to the locus where selectivity is desired a composition comprising (a) an herbicidally effective amount of a pyrrolidone compound of the formula

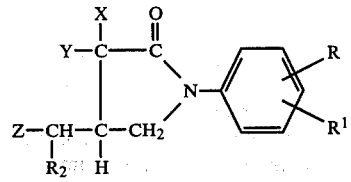

in which
X is hydrogen, chlorine or methyl;
Y is hydrogen, chlorine, or bromine;

Z is chlorine or bromine;

R is hydrogen, alkyl, acetyl, chlorine, bromine, fluorine, iodine, trifluoromethyl, nitro, cyano, alkoxy, alkylthio, alkylsulfinyl, alkysulfonyl, trifluoromethylthio, trifluoromethylsulfinyl, trifluoromethylsulfonyl, pentafluoropropionamido, or 3-methylureido;

$R_1$ is hydrogen, alkyl, chlorine, or trifluoromethyl; and, $R_2$ is alkyl or hydrogen; and, (b) a non-phytotoxic antidotally effective amount of a compound of the formula

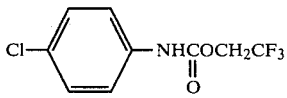

The locus where selectivity is desired may include soil, seeds, seedlings, and vegetation.

Preparation

The pyrrolidone compounds of the present invention can be prepared by the procedures described in U.S. Pat. No. 4,110,105.

The trifluoromethyl p-chlorophenylcarbamate compound of this invention may be prepared according to the following procedure.

Two and one-half grams (2.5 g) (0.025 mole) of 2,2,2-trifluoroethanol, 25 milliliters (ml) of trichloromethane, 3,8 g (0.025 mole) of p-chlorophenylisocyanate, 3, drops of triethylamine and 1 drop of dibutyltindilaurate were combined, stirred at room temperature for 15 minutes, refluxed for two hours, cooled and evaporated. Yield was 6.1 g of 2,2,2-trifluoroethyl p-chlorophenyl carbamate. m.p.=54°-57° C. Structure was confirmed by infrared spectroscopy.

Testing

A stock solution of the pyrrolidone was prepared by diluting the requisite amount of the herbicide in water or in an acetone-water solution. Examples of solution compositions and application rates are summarized in Table I.

TABLE I

| | Herbicide Stock Solutions | | | | |
|---|---|---|---|---|---|
| | Composition | | | Application | |
| Herbicide Name | Herbicide (mg)* | Water (ml) | Acetone (ml) | ml/flat** | lb/acre |
| 1-m-trifluoromethylphenyl-3-chloro-4-chloromethyl-2-pyrrolidone | 781 | 100 | — | | 1.25 |
| | 122 | 20 | 20 | 0.5 | |

*The weight is measured in terms of mg of formulated herbicide.
**The flats measure 5.95 inches by 9.5 inches. Approximately four (4) mg/flat is equal to one (1) lb/acre.

In each case, the herbicide was applied to the soil after planting seeds and prior to emergence of plants. The herbicide was applied to the soil alone prior to pre-emergence surface application of the antidote or following in-furrow application of the antidote.

Stock solutions of the antidote compound were prepared at the desired concentrations by diluting the requisite amount in acetone or in an acetone-water solution. Examples of solution compositions, rates and application methods are summarized in Table II.

TABLE II

| Antidote Stock Solutions | | | | | |
|---|---|---|---|---|---|
| Antidote: Diallyl dichloroacetamide | | | | | |
| Composition | | Water | Application | | Method |
| Antidote (mg) | Acetone (ml) | (ml) | ml/flat | lb/acre | |
| 95 | 15 | — | 0.30 | 1.00 | IF* |
| 95 | 15 | — | 1.50 | 5.00 | IF |
| 60 | 20 | 20 | | 1.00 | PES** |
| 300 | 20 | 20 | | 5.00 | PES |

*IF = In-furrow surface application of antidote.
**PES = Pre-emergent surface application.

The antidote solutions were applied to the soil either by in-furrow surface application or by pre-emergence surface application.

For in-furrow application, a one pint (473 cubic centimeter (cc)) sample of soil containing the previously incorporated herbicide was removed and retained from each planting flat. After leveling and furrowing the soil, seeds of the crop or weed species were planted ½ inch deep (1.27 centimeter). Each flat was divided in half by a wooden barrier. A stock solution of the antidote was atomized directly onto the exposed seeds and soil in the open furrow on one side of the barrier. The seeds in the entire flat were then covered with the previously removed soil. The antidotally untreated sections of flats were compared for observed differences which would indicate lateral movement of the antidote through the soil.

Control flats contained crops treated with herbicide only. All flats were placed on greenhoused benches where temperature was maintained between 70° and 90° F. (21.1° to 32.2° C.). The flats were watered by sprinkling as needed to assure good plant growth.

All of the soil used in the tests described herein was loamy sand soil treated with 50 parts per million (ppm) each of a commercially available fungicide, N-[(trichloromethyl)-thio]-4-cyclohexene-1,2dicarboximide, and 18-18-18 fertilizer, which contains 18% by weight equivalent each of nitrogen, phosphorus pentoxide, and potassium oxide.

Injury ratings were taken four weeks after application of the antidote. The effectiveness of the antidote was determined by visual comparison of crop injury which occurred in the test flats to that which occurred in the control flats.

The treated crops initially screened for diminution of herbicidal injury were milo, wheat, cotton, rice, barley, corn and soybeans. The compounds were also tested on weed species. The weed species tested included watergrass (*Echinochloa crusgalli*), foxtail (*Setaria viridis*), wild oat (*Avena fatua*) and mustard (*Brassica spp.*)

KEY TO TABLES III AND IV

Herbicide 1-m-Trifluoromethylphenyl-3-chloro-4-chloromethyl-2-pyrrolidone

Application Methods

IF = In-furrow surface application of antidote (soil subsequently treated with herbicide only).

PES = Pre-emergence surface application of herbicide or antidote.

TM = Tank mixed solution of herbicide and antidote.

If no antidote was applied, the word "none" appears in the Antidote Rate column. The results shown on this line are the percent injuries sustained by each of the crops when treated with the herbicide only at the rate specified.

All rates shown, for both herbicide and antidote, are in pounds per acre.

Injury Ratings.

The injury to the crops (Table III) or weeds (Table IV) is shown as a percentage of damage done to the plants as compared to an evaluation of the overall undamaged state of the plants. The damage done to the plants is a function of the number of plants injured and the extend of injury to each plant. This rating is made four (4) weeks after application of the herbicide alone or of the herbicide in combination with the antidote.

An asterisk (*) in Table III indicates that the antidote compound is active in reducing herbicidal injury to the crop.

Table IV shows the antidote compounds tested have no effect on weeds, i.e., herbicidal injury to the weeds is sustained even in the presence of the antidote compound.

TABLE IV

Herbicidal Effectiveness

|  |  | Antidote |  | Percent Injury | | |
|---|---|---|---|---|---|---|
| Herbicide | Rate | Rate | Method | Mustard | Water-grass | Fox-tail |
| 1-m-trifluoro- | 0.50 | none | — | 80 | 90 | 100 |
| methylphenyl-3- | 0.50 | 1.00 | IF | 80 | 90 | 100 |
| chloromethyl-2- | 0.50 | 2.00 | IF | 80 | 90 | 100 |
| pyrrolidone | 0.50 | 5.00 | IF | 80 | 90 | 100 |
|  | 0.50 | none | — | 80 | 90 | 100 |
|  | 0.50 | 1.00 | PES/TM | 80 | 80 | 100 |
|  | 0.50 | 2.00 | PES/TM | 80 | 90 | 100 |
|  | 0.50 | 5.00 | PES/TM | 80 | 80 | 100 |
|  | 0.75 | none | — | 85 | 100 | 100 |
|  | 0.75 | 1.00 | IF | 85 | 100 | 100 |
|  | 0.75 | 2.00 | IF | 85 | 100 | 100 |
|  | 0.75 | 5.00 | IF | 85 | 100 | 100 |
|  | 0.75 | none | — | 85 | 100 | 100 |
|  | 0.75 | 1.00 | PES/TM | 85 | 100 | 100 |
|  | 0.75 | 2.00 | PES/TM | 85 | 100 | 100 |
|  | 0.75 | 5.00 | PES/TM | 85 | 100 | 100 |
|  | 1.00 | none | — | 100 | 100 | 100 |
|  | 1.00 | 1.00 | IF | 100 | 100 | 100 |
|  | 1.00 | 2.00 | IF | 100 | 100 | 100 |
|  | 1.00 | 5.00 | IF | 100 | 100 | 100 |

TABLE III

Antidotal Effectiveness

| Herbicide Name | Rate | Antidote Rate | Method | Milo % Inj | Wheat % Inj | Cotton % Inj | Rice % Inj | Barley % Inj | Corn % Inj | Soybean % Inj |
|---|---|---|---|---|---|---|---|---|---|---|
| 1-m-trifluoromethyl- | 1.25 | none | — |  | 100 | 70 | 100 | 100 |  |  |
| phenyl-3-chloro- | 1.25 | 5.00 | IF |  | *35 | *60 | *85 | *70 |  |  |
| 4-chloromethyl- |  |  |  |  |  |  |  |  |  |  |
| 2-pyrrolidone | 0.50 | none | — | 90 |  |  |  |  | 75 | 65 |
|  | 0.50 | 5.00 | IF | *65 |  |  |  |  | *65 | 65 |
|  | 1.25 | none | — |  | 90 | 65 | 98 | 100 |  |  |
|  | 1.25 | 5.00 | IF |  | *35 | *50 | *55 | *90 |  |  |
|  | 0.50 | none | — | 65 |  |  |  |  | 65 | 60 |
|  | 0.50 | 5.00 | IF | *55 |  |  |  |  | 65 | 60 |
|  | 1.00 | none | — |  | 100 | 55 | 100 | 100 |  |  |
|  | 1.00 | 5.00 | IF |  | 100 | *40 | 100 | 100 |  |  |
|  | 0.50 | none | — | 100 |  |  |  |  | 85 | 100 |
|  | 0.50 | 5.00 | IF | 100 |  |  |  |  | *60 | 100 |
|  | 1.00 | none | — |  | 100 | 55 | 100 | 100 |  |  |
|  | 1.00 | 5.00 | IF |  | 100 | *40 | 100 | 100 |  |  |
|  | 0.50 | none | — | 100 |  |  |  |  | 85 | 90 |
|  | 0.50 | 5.00 | IF | 100 |  |  |  |  | *60 | 100 |
|  | 0.50 | none | — |  | 10 |  |  |  |  |  |
|  | 0.50 | 1.00 | IF |  | 10 |  |  |  |  |  |
|  | 0.50 | 2.00 | IF |  | *0 |  |  |  |  |  |
|  | 0.50 | 5.00 | IF |  | *0 |  |  |  |  |  |
|  | 0.50 | none | — |  | 10 |  |  |  |  |  |
|  | 0.50 | 1.00 | PES/TM |  | *0 |  |  |  |  |  |
|  | 0.50 | 2.00 | PES/TM |  | *0 |  |  |  |  |  |
|  | 0.50 | 5.00 | PES/TM |  | *0 |  |  |  |  |  |
|  | 0.75 | none | — |  | 20 |  |  |  |  |  |
|  | 0.75 | 1.00 | IF |  | *10 |  |  |  |  |  |
|  | 0.75 | 2.00 | IF |  | *0 |  |  |  |  |  |
|  | 0.75 | 5.00 | IF |  | *0 |  |  |  |  |  |
|  | 0.75 | none | — |  | 20 |  |  |  |  |  |
|  | 0.75 | 1.00 | PES/TM |  | *0 |  |  |  |  |  |
|  | 0.75 | 2.00 | PES/TM |  | *0 |  |  |  |  |  |
|  | 0.75 | 5.00 | PES/TM |  | *0 |  |  |  |  |  |
|  | 1.00 | none | — |  | 35 |  |  |  |  |  |
|  | 1.00 | 1.00 | IF |  | *25 |  |  |  |  |  |
|  | 1.00 | 2.00 | IF |  | *25 |  |  |  |  |  |
|  | 1.00 | 5.00 | IF |  | *20 |  |  |  |  |  |
|  | 1.00 | none | — |  | 35 |  |  |  |  |  |
|  | 1.00 | 1.00 | PES/TM |  | *10 |  |  |  |  |  |
|  | 1.00 | 2.00 | PES/TM |  | *10 |  |  |  |  |  |
|  | 1.00 | 5.00 | PES/TM |  | *0 |  |  |  |  |  |
|  | 2.00 | none | — |  | 65 |  |  |  |  |  |
|  | 2.00 | 1.00 | IF |  | 65 |  |  |  |  |  |
|  | 2.00 | 2.00 | IF |  | 65 |  |  |  |  |  |
|  | 2.00 | 5.00 | IF |  | *40 |  |  |  |  |  |
|  | 2.00 | none | — |  | 65 |  |  |  |  |  |
|  | 2.00 | 1.00 | PES/TM |  | *30 |  |  |  |  |  |
|  | 2.00 | 2.00 | PES/TM |  | *30 |  |  |  |  |  |
|  | 2.00 | 5.00 | PES/TM |  | *30 |  |  |  |  |  |

TABLE IV-continued

Herbicidal Effectiveness

| Herbicide | | Antidote | | Percent Injury | | |
|---|---|---|---|---|---|---|
| | Rate | Rate | Method | Mustard | Water-grass | Foxtail |
| | 1.00 | none | — | 100 | 100 | 100 |
| | 1.00 | 1.00 | PES/TM | 100 | 100 | 100 |
| | 1.00 | 2.00 | PES/TM | 100 | 100 | 100 |
| | 1.00 | 5.00 | PES/TM | 100 | 100 | 100 |
| | 2.00 | none | — | 100 | 100 | 100 |
| | 2.00 | 1.00 | IF | 100 | 100 | 100 |
| | 2.00 | 2.00 | IF | 100 | 100 | 100 |
| | 2.00 | 5.00 | IF | 100 | 100 | 100 |
| | 2.00 | none | — | 100 | 100 | 100 |
| | 2.00 | 1.00 | PES/TM | 100 | 100 | 100 |
| | 2.00 | 2.00 | PES/TM | 100 | 100 | 100 |
| | 2.00 | 5.00 | PES/TM | 100 | 100 | 100 |

Test Results

The composition of pyrrolidone herbicide and antidote compound was effective for the reduction of herbicidal injury to a wide variety of crops. Use of the antidote compound did not result in a reduction of herbicidal injury to weeds.

Formulations

A formulation is the incorporation of a formulant in a form which is directly usable on crops and weeds. As defined herein, a "formulant" is the material which is to be formulated. The formulant may be either an antidote compound alone or an herbicide and antidote composition. The purpose of the formulation is to apply the formulant to the locus where it is desired to establish herbicial selectivity by a convenient method. The "locus" may include soil, seeds, seedlings and vegetation.

The formulations are commonly dusts, wettable powders, granules, solutions or emulsifiable concentrates.

Dusts are free-flowing powder compositions containing the formulant impregnated on a particulate carrier. The particle size of the carriers is usually in the approximate range of 30 to 50 microns. Examples of suitable carriers are talc, bentonite, diatomaceous earth, and pyrophyllite. The composition generally contains up to 50% of formulant. Anti-caking and anti-static agents may also be added. Dusts may be applied by spraying from boom and hand sprayers on airplanes.

Wettable powders are finely divided compositions comprising a particulate carrier impregnated with the formulant and additionally containing one or more surface active agents. The surface active agent promotes rapid dispersion of the powder in an aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols, in which the alcohol groups are free, omega-substituted polyethylene glycols of relatively long chain length. A list of surface active agents suitable for use in agriculture formulations can be found in Wade Van Valkenburg, *Pesticide Formulations* (Marcel Dekker, Inc., N.Y., 1973) at pages 79-84.

Granules comprise the formulant impregnated on a particulate inert carrier having a particle size of about 1 to 2 millimeters (mm) in diameter. The granules can be made by spraying a solution of the formulant in a volatile solvent onto the granular carrier. Examples of suitable carriers for the preparation of granules include clay, vermiculite, sawdust, and granular carbon.

Emulsifiable concentrates consist of an oil solution of the formulant plus an emulsifying agent. Prior to use the concentrate is diluted with water to form a suspended emulsion of oil droplets. The emulsifiers used are usually a mixture of anionic and nonionic surfactants. Other additives, such as suspending agents and thickeners, may be included in the emulsifiable concentrate.

When the formulant is an antidote and herbicide composition, the proportion of antidote compound to herbicide compound generally ranges from approximately 0.001 to 30 parts by weight of the antidote compound per weight of the herbicide compound.

Formulations generally contain several additives in addition to the formulant and carrier or agent. Among these are inert ingredients, diluent carriers, organic solvents, water, oil and water, water in oil emulsions, carrier of dusts and granules, and surface active wetting, dispersing and emulsifying agents. Fertilizers, e.g., ammonium nitrate, urea and superphosphate, may be included. Aids to rooting and growth, e.g., compost, manure, humus and sand, may also be included.

Alternatively, the antidote compounds and herbicide and antidote compositions of this invention can be applied to a crop by addition of the formulant to irrigation water supplied to the field to be treated. This method of application permits the penetration of the compositions into the soil as the water is absorbed.

As another alternative, the formulant can be applied to the soil in the form of a solution in a suitable solvent. Solvents frequently used in these formulations include kerosene, fuel oil, xylene, petroleum fractions with boiling ranges above xylene and aromatic petroleum fractions rich in methylated naphtalenes. Liquid solutions, like dusts, may be applied by spraying from boom and hand sprayers on airplanes.

What is claimed is:

1. A composition comprising:
(a) an herbicidally effective amount of a pyrrolidone compound of the formula $$\begin{array}{c} X \quad O \\ | \quad \| \\ Y-C-C \\ | \quad \quad \searrow N - \bigcirc - R \\ Z-CH-C-CH_2 \quad \quad R^1 \\ | \quad | \\ R_2 \quad H \end{array}$$

in which
X is hydrogen, chlorine or methyl;
Y is hydrogen, chlorine, or bromine;
Z is chlorine or bromine;
R is hydrogen, alkyl, acetyl, chlorine, bromine, fluorine, iodine, trifluoromethyl, nitro, cyano, alkoxy, alkylthio, alkylsulfinyl, alkylsulfonyl, trifluoromethylthio, trifluoromethylsulfinyl, trifluoromethylsulfonyl, pentafluoropropionamido, or 3-methylureido;
$R_1$ is hydrogen, alkyl, chlorine, or trifluoromethyl; and,
$R_2$ is alkyl or hydrogen; and,
(b) a non-phytotoxic antidotally effective amount of a compound of the formula

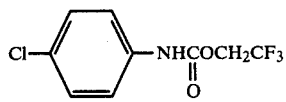

2. A composition as defined in claim 1 wherein X is hydrogen, Y is chlorine, Z is chlorine, R is m-trifluoromethyl, $R_1$ is hydrogen, and $R_2$ is hydrogen.

3. A method of controlling undesirable vegetation and reducing pyrrolidone-type herbicidal crop injury comprising applying to the locus where control is desired an herbicidally effective amount of a composition comprising:

(a) an herbicidally effective amount of a pyrrolidone compound of the formula in which
X is hydrogen, chlorine or methyl;
Y is hydrogen, chlorine, or bromine;
Z is chlorine or bromine;
R is hydrogen, alkyl, acetyl, chlorine, bromine, fluorine, iodine, trifluoromethyl, nitro, cyano, alkoxy, alkylthio, alkylsulfinyl, alkylsulfonyl, trifluoromethylthio, trifluoromethylsulfinyl, trifluoromethylsulfonyl, pentafluoropropionamido, or 3-methylureido;
$R_1$ is hydrogen, alkyl, chlorine, or trifluoromethyl; and,
$R_2$ is alkyl or hydrogen; and, (b) a non-phytotoxic antidotally effective amount of a compound of the formula

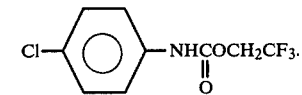

4. A method as defined in claim 3 wherein X is hydrogen, Y is chlorine, Z is chlorine, R is m-trifluoromethyl, $R_1$ is hydrogen, and $R_2$ is hydrogen.

* * * * *